United States Patent [19]

Austermühle-Bertola

[11] 4,211,720
[45] Jul. 8, 1980

[54] PREPARATION OF CYANO-SUBSTITUTED CYCLOPROPANE DERIVATIVES

[75] Inventor: Helena Austermühle-Bertola, Amsterdam, Netherlands

[73] Assignee: Shell International Research Maatschappij B.V., Netherlands

[21] Appl. No.: 910,779

[22] Filed: May 30, 1978

[51] Int. Cl.² .................. C07C 120/00; C07C 121/48
[52] U.S. Cl. .................................. 260/464; 260/465.4
[58] Field of Search .......................................... 260/464

[56] References Cited

U.S. PATENT DOCUMENTS

| | | | |
|---|---|---|---|
| 3,658,879 | 4/1972 | Julia | 560/124 |
| 4,000,180 | 12/1976 | Punja | 260/464 X |
| 4,113,969 | 9/1978 | Lantzsch | 560/124 |

FOREIGN PATENT DOCUMENTS

| | | |
|---|---|---|
| 2574510 | 4/1976 | Fed. Rep. of Germany . |
| 2552615 | 6/1976 | Fed. Rep. of Germany . |
| 50-89508 | 7/1975 | Japan . |
| 51-55484 | 5/1976 | Japan . |
| 52-14750 | 7/1976 | Japan . |

OTHER PUBLICATIONS

Kondo, C. A., 85 (1976), 176937e.
Szmant, "Organic Chemistry", Prentice Hall, 1957, pp. 405–406.
Royals, "Advanced Organic Chemistry", Prentice Hall, 1956, pp. 106–109.
Weygand/Hilgetag, "Preparative Organic Chemistry", John Wiley & Son, 1972, pp. 1003–1007.

*Primary Examiner*—Joseph P. Brust
*Attorney, Agent, or Firm*—Pravel, Gambrell, Hewitt, Kirk, Kimball & Dodge

[57] ABSTRACT

A novel process is disclosed for the preparation of cyano-substituted cyclopropane derivatives of the following general formula:

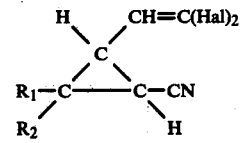

wherein $R_1$, $R_2$ and Hal have the meanings given in the description. The process comprises the steps of cyclizing and dehydrohalogenating, in the presence of a base, a 4,6,6,6-tetrahalo-2-cyano-3,3-dialkylhexanoic acid or an alkyl ester thereof, followed by thermal decarboxylation of the resulting cyclized and dehydrohalogenated product. Under selected conditions cyclization, dehydrohalogenation and decarboxylation occur simultaneously in one reaction zone. The resulting cyano-substituted cyclopropane derivatives are useful as intermediates in the production of insecticidally active compounds.

7 Claims, No Drawings

PREPARATION OF CYANO-SUBSTITUTED CYCLOPROPANE DERIVATIVES

BACKGROUND OF THE INVENTION

The cyano-substituted cyclopropane derivatives of the present invention are useful intermediates in the manufacture of 2-(2,2-dihalovinyl)-3,3-dialkylcyclopropanecarboxylic acids and their corresponding alkyl esters which are themselves key intermediates in the manufacture of a group of compounds known as "synthetic pyrethoids" which exhibit remarkable levels of insecticidal and acaricidal activity. U.K. Pat. No. 1,413,491 discloses and claims in important group of these synthetic pyrethoids, for example, the 3-phenoxybenzyl ester of 2-(2,2-dichlorovinyl)-3,3-dimethylcyclopropanecarboxylic acid is an insecticidally active compound. An examination of U.K. Pat. No. 1,413,491 demonstrates the difficulty in synthesizing the carboxylic acid precursors employed in the preparation of the insecticidally active compounds. One method employed comprises the ozonolysis of an ester of chrysanthemic acid, the product of ozonolysis is then used in a Wittig reaction to generate the desired dihalovinyl substituted cyclopropane carboxylate. This difficulty in synthesizing the appropriate cyclopropane carboxylic acid precursors has prompted other researchers to expend considerable effort in attempting to find a simpler route to the synthesis of the above-mentioned cyclopropanecarboxylic acid—see for example Netherlands patent application 7,510,479 and 7,509,631—and, so far, all published routes to this acid are cumbersome and involve many process steps.

The Applicant has discovered the following key intermediates for the simple manufacture of the above-mentioned desired acids:

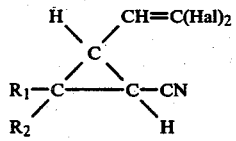

wherein for the production of 2-(2,2-dichlorovinyl)-3,3-dimethylcyclopropanecarboxylic acid Hal represent chlorine and $R_1$ and $R_2$ represent methyl, and for the production of other cyclopropanecarboxylic acid precursors useful in the process described in U.K. Pat. No. 1,413,491 Hal represents a fluorine, chlorine or bromine atom and $R_1$ and $R_2$ each, independently, represent an alkyl group of one to four carbon atoms. It will be appreciated that the above-defined intermediates can be readily converted by known methods, such as, for example, hydrolysis of the cyano group, into the corresponding cyclopropanecarboxylic acid and/or their corresponding alkyl esters.

SUMMARY OF THE INVENTION

The present invention therefore provides a process for the preparation of new cyano-substituted cyclopropane derivatives of general formula:

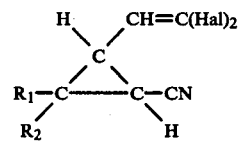

wherein Hal represents a fluorine, chlorine or bromine atom and $R_1$ and $R_2$ each, independently, represents an alkyl group of one to four atoms, preferably methyl; which comprises:

(a) cyclizing and dehydrohalogenating, by contacting with a base, a compound of general formula:

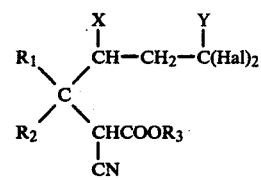

wherein X and Y each represents a chlorine or bromine atom and $R_3$ represents a hydrogen atom or an alkyl group of one to four carbon atoms; and (b) thermally decarboxylating the resulting cyclized dehydrohalogenated product to form the compound of general formula II.

DESCRIPTION OF THE PREFERRED EMBODIMENT

The starting material of the present invention, a 4,6,6,6-tetrahalo-2-cyano-3,3-dialkylhexanoic acid or a corresponding alkyl ester thereof, may be conveniently made in accordance with the method disclosed in copending U.S. Patent Application Ser. No. 813,433, filed July 7, 1977, entitled "2-CYANOHEXANOIC ACID DERIVATIVES", the disclosure of which is hereby incorporated by reference as a part of this disclosure. Of course, although U.S. Ser. No. 813,433 discloses only the method by which the hexanoic acid compounds may be made it is to be realized that corresponding alkyl esters thereof may be prepared by known methods, as for example, esterification methods.

In step (a) of the process according to the invention mild temperatures, e.g. ambient temperatures, are suitable to effect the cyclization and dehydrohalogenation but the reaction will take place at temperatures in the range 30° to about 160° C. Higher than ambient temperatures are generally preferred in order to achieve shorter reaction times, e.g. temperatures in the range 60°–100° C. Generally speaking, cyclization and dehydrohalogenation takes place simultaneously but if very mild conditions are employed, for example a 1%w solution of hydroxide in methanol 20°–30° C., an intermediate cyclopropane derivative of the following general formula is predominantly produced:

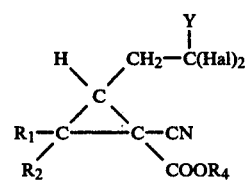

wherein $R_1$, $R_2$ and Y have the meanings hereinbefore specified; and $R_4$ is a hydrogen or alkali metal or alkaline earth metal atom, an ammonium or alkyl-substituted ammonium, or an alkyl group of one to four carbon atoms. Compounds of the general formula IV are novel compounds and accordingly represent a novel intermediate in the process according to the invention.

The cyclization and dehydrohalogenation step has to be carried out by contact of the starting compound with a base and, in general, mild bases are sufficient, for example alkali metal and alkaline earth metal and ammonium hydroxides, acetates, carbonates, bicarbonates; and nitrogenous bases such as ammonia and alkyl-substituted ammonias e.g. primary, secondary and tertiary amines. Good results have also been obtained with alkali metal acetates, carbonates and bicarbonates. Particularly preferred bases are ammonia and sodium acetate.

Step (a) is preferably carried out in the absence of water and in the presence of a non-aqueous solvent— e.g. an alkanol, such as methanol or ethanol, or dimethyl formamide. The latter solvent has been found to be particularly useful.

Step (b), the decarboxylation step in the process according to the invention, is preferably effected at a temperature in the range of from about 100° to about 150° C. and it has been found that decarboxylation proceeds smoothly when the free acid, the ammonium salt or the alkali metal salt is employed. Advantageously, a polar aprotic solvent, e.g. dimethyl formamide, is used in the decarboxylation step.

Generally, step (a) and (b) may be carried out at ambient pressures, although super atmospheric pressures may be employed if desired.

Surprisingly it has been found that step (a) and step (b) can be carried out in the same reaction zone or pot and that the two steps appear to take place simultaneously, that is to say cyclization, dehydrohalogentaion and decarboxylation all appear to be taking place at the same time. Such a combination of chemical reactions renders this aspect of the process according to the invention particularly valuable as an improvement in the route to the important pyrethroid insecticide intermediate, 2-(2,2-dichlorovinyl)-3,3-dimethylcyclopropanecarboxylic acid. As might be expected, the conditions required to achieve this combination of reactions have to be carefully selected in order to obtain maximum yields of the end-product.

According to a preferred aspect of the invention, therefore, the process is carried out in one reaction zone, or pot, in the presence of a nitrogenous base and an inert non-aqueous solvent at a temperature in the range 70° to 160° C., preferably in the range 80° to 150° C. Better results have been obtained with ammonia or sodium acetate as the base and dimethyl formamide or N-methyl-pyrollidone as the inert non-aqueous solvent. Also anhydrous conditions should preferably be employed.

The cyano-substituted cyclopropane derivatives may be recovered from the reaction mixture by any suitable method, and, if desired, purified by known methods.

Those compounds of general formula IV are novel compounds and as such are included within the scope of the invention. A particular preferred novel compound is 1-cyano-2-(2,2-dichlorovinyl)-3,3-dimethylcyclopropanecarboxylic acid together with the alkali metal, alkaline earth metal and ammonium and substituted ammonium salts thereof. These derivatives are useful intermediates in the preparation of 2-(2,2-dichlorovinyl)-3,3-dimethylcyclopropanecarboxylic acid, certain esters of which possess insecticidal activity.

The invention is further illustrated in the following Examples.

EXAMPLE I Preparation of 2-(2,2-dichlorovinyl)-3,3-dimethylcyclopropane nitrile (A)

Step (a) Preparation of 1-cyano-2-(2,2-dichlorovinyl)-3,3-dimethylcyclopropanecarboxylic acid (B)

Methyl 4-bromo-2-cyano-3,3-dimethyl-6,6,6-trichlorohexanoate (64.0 g, 0.166 m) was added over a period of 25 minutes to a suspension of potassium hydroxide (120.0 g, 1,8 m) in methanol (2100 ml) at 20° C. The mixture was then stirred for 1 hour at 35° C. and subsequently heated under reflux for 2.5 hours. The solvent was then removed under reduced pressure and the residue was dissolved in water (1500 ml). The aqueous phase was washed once with dichloromethane and acidified with concentrated hydrochloric acid to about pH 1. The mixture was then extracted three time with dichloromethane and the extracts were dried. The solvent was removed under reduced pressure to yield the required acid 1-cyano-2-(2,2-dichlorovinyl)-3,3-dimethylcyclopropanecarboxylic acid, as a white crystalline solid (m.p. 128°–132° C., yield 37.6 g, 97%). The NMR spectrum of the compound measured at 60 MHz in deuterochloroform solution showed the following absorptions relative to a tetramethylsilane standard. On the basis of the spectrum it was established that the product consisted of two geometric isomers, Z and E, in the ratio Z:E=56:44.

$\delta$=6.10 ppm (doublet, —CH=Z-isomer)
$\delta$=5.78 ppm (doublet, —CH=E-isomer)
$\delta$=2.83 ppm (doublet, ring H E-isomer)
$\delta$=2.65 ppm (doublet, ring H Z-isomer)
$\delta$=1.60, 1.38 ppm (singlets, two $CH_3$ Z-isomer)
$\delta$=1.47, 143 ppm (singlets, two $CH_3$ E-isomer)

Step (b) Thermal decarboxylation of (B)

1-Cyano-2-(2,2-dichlorovinyl)-3,3-dimethylcyclopropanecarboxylic acid (1.5 g) was dissolved in dimethylformamide (10 ml) and the solution was saturated with gaseous ammonia at 20° C. The solution was then stirred at 130° C. for 18 hours, then diluted with water (150 ml) and extracted with pentane. The extracts were dried ($MgSO_4$) and the solvent was removed under reduced pressure to give the required 2-(2,2-dichlorovinyl)-3,3-dimethylcyclopropane nitrile, yield 82%.

EXAMPLE II

The procedure of Example I was repeated using methyl 4-chloro-2-cyano-3,3-dimethyl-6,6,6-trichlorohexanoate as starting material. The yield of 1-cyano-2-(2,2-dichlorovinyl)-3,3-dimethylcyclopropanecarboxylic acid was 95–96%. cl EXAMPLE III Preparation of (A) in one reaction vessel using $NH_3$ as base 4-Chloro-2-cyano-3,3-dimethyl-6,6,6-trichlorohexanoic acid (40 g) was dissolved in dimethyl formamide (66 ml) and the solution, at room temperature, was saturated with gaseous ammonia with no external cooling. The solution was stirred at 140° C. for 5 hours, then diluted with water and extracted with ether (3×100 ml). The ether solution was washed with saturated NaCl, dried over MgSO$_4$ and evaporated to afford Compound A as a yellow oil (purity 85%) which partly crystallized on standing. Yield 79%.

EXAMPLE IV Preparation of (A) in one reaction vessel using Na Acetate as base 4-Chloro-2-cyano-3,3-dimethyl-6,6,6-trichlorohexanoic acid (3.07 g) and sodium acetate (2.05 g; water-free) were dissolved in dimethyl formamide (8.0 ml). The solution was then stirred at 145° C. for 12 hours. The working-up procedure was the same as indicated in Example III and yielded 1.85 g of Compound A with purity 90%. Yield 86%.

EXAMPLE V Preparation of (A) in one reaction vessel using ammonia under pressure as base A solution of 4-chloro-2-cyano-3,3-dimethyl-6,6,6-trichlorohexanoic acid (6.14 g) in dimethyl formamide (12 ml) was stirred at 145° C. for 4 hours under an ammonia atmosphere at initially 5 bar pressure. After release of the pressure the mixture was stirred for another 6 hours at 145° C. After cooling, over 90% of the solvent was flashed off (bath temperature max. 60° C., pressure 12 mmHg). The residue was mixed with toluene and subsequently washed with aqueous hydrochloric acid and aqueous sodium bicarbonate. After drying of the organic phase the solvent was removed under reduced pressure to yield 3.3 g of the required 2-(2,2-dichlorovinyl)-3,3-dimethylcyclopropane nitrile (97% pure, 89% yield).

EXAMPLE VI Preparation of (A) in one reaction vessel using N,N-diisopropyl-N-ethylamine as base A solution of 4-chloro-2-cyano-3,3-dimethyl-6,6,6-trichlorohexanoic acid (2.5 g) and N,N-diisopropyl-N-ethylamine (2.6 g) in dimethyl formamide (25 ml) was heated at 145° C. for 5 hours. After cooling to room temperature the reaction mixture was worked up as indicated in Example III. This yielded 1.4 g of the required 2-(2,2-dichlorovinyl)-3,3-dimethylcyclopropane nitrile with purity 79%. Yield 73%.

From the foregoing, those of ordinary skill in the art may make modification and variations of the practice of the invention without departing from the scope of the invention as claimed herein.

I claim:

1. A process for preparing cyano-substituted derivatives of general formula

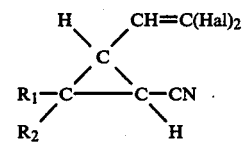

wherein Hal represents a flourine, chlorine or bromine atom and R$_1$ and R$_2$ each independently represent an alkyl group of one to four carbon atoms, which comprises contacting a compound of general formula

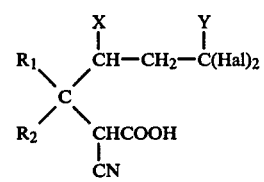

wherein X and Y each independently represents a chlorine or bromine atom under anhydrous conditions with a base and a polar aprotic solvent at temperatures from about 100° C. to about 150° C.

2. The process of claim 1 wherein R$_1$ and R$_2$ are methyl groups.

3. The process of claim 1 wherein the base employed is a nitrogenous base or an alkali metal acetate, carbonate or bicarbonate.

4. The process of claim 1 wherein the base employed is ammonia or sodium acetate.

5. The process of claim 1 in which the polar aprotic solvent is dimethyl formamide.

6. The process of claim 1 wherein the base is ammonia and the polar aprotic solvent is dimethyl formamide.

7. The process of claim 1 wherein the base is a nitrogenous base.

* * * * *